United States Patent
Kim et al.

(10) Patent No.: US 11,944,948 B2
(45) Date of Patent: Apr. 2, 2024

(54) COMPOSITE FOR FORMING COACERVATE INTERFACIAL FILM, PICKERING EMULSION CONTAINING THE SAME, AND METHOD FOR PRODUCING THE SAME

(71) Applicants: RESEARCH & BUSINESS FOUNDATION SUNGKYUNKWAN UNIVERSITY, Suwon-si (KR); SUNJIN BEAUTY SCIENCE CO., LTD., Seoul (KR)

(72) Inventors: Jin Woong Kim, Seongnam-si (KR); Yeong Sik Cho, Suwon-si (KR); Ji Woo Bae, Seoul (KR); Hye Min Seo, Hanam-si (KR); Kyoung Hee Shin, Bucheon-si (KR); Sung Ho Lee, Seoul (KR)

(73) Assignees: RESEARCH & BUSINESS FOUNDATION SUNGKYUNKWAN UNIVERSITY, Gyeonggi-Do (KR); SUNJIN BEAUTY SCIENCE CO., LTD., Seoul (KR)

( * ) Notice: Subject to any disclaimer, the term of this patent is extended or adjusted under 35 U.S.C. 154(b) by 0 days.

(21) Appl. No.: 17/740,674

(22) Filed: May 10, 2022

(65) Prior Publication Data
US 2022/0362732 A1     Nov. 17, 2022

(30) Foreign Application Priority Data

May 11, 2021    (KR) ........................ 10-2021-0060805

(51) Int. Cl.
| | | |
|---|---|---|
| *B01J 13/10* | (2006.01) | |
| *A61K 8/06* | (2006.01) | |
| *A61K 9/107* | (2006.01) | |
| *B82Y 5/00* | (2011.01) | |

(52) U.S. Cl.
CPC .............. *B01J 13/10* (2013.01); *A61K 8/064* (2013.01); *A61K 9/107* (2013.01); *B82Y 5/00* (2013.01)

(58) Field of Classification Search
CPC ....................................................... B01J 13/10
See application file for complete search history.

(56) References Cited

U.S. PATENT DOCUMENTS

2019/0231658 A1* 8/2019 Lei ........................... A61K 8/43

* cited by examiner

*Primary Examiner* — Dah-Wei D. Yuan
*Assistant Examiner* — Andrew J Bowman
(74) *Attorney, Agent, or Firm* — Harness, Dickey & Pierce, P.L.C.

(57) ABSTRACT

Disclosed is a composite for forming a coacervate interfacial film. The composite for forming the coacervate interfacial film contains a cationic hectorite nanoplate-shaped particle structure containing a hectorite nanoplate-shaped particle and a cationic surfactant coupled to a surface of the hectorite nanoplate-shaped particle, and an anionic cellulose nanofibril containing an anionic functional group in at least a portion thereof, in which the composite may form the coacervate interfacial film at an interface of an oil phase and a water phase through electrostatic interaction between the cationic surfactant and the anionic functional group.

10 Claims, 4 Drawing Sheets

COMPOSITE FOR FORMING COACERVATE INTERFACIAL FILM, PICKERING EMULSION CONTAINING THE SAME, AND METHOD FOR PRODUCING THE SAME

CROSS-REFERENCE TO RELATED APPLICATION

This application claims the benefit and priority of Korean Patent Application No. 10-2021-0060805 filed on May 11, 2021. The entire disclosure of the above application is incorporation herein by reference.

FIELD

The present disclosure relates to a composite capable of forming a coacervate interfacial film at an interface of an emulsion containing two or more phases, a Pickering emulsion containing the same, and a method for producing the same.

BACKGROUND

This sections provides background information related to the present disclosure which is not necessarily prior art.

As the technology of the dermatological industry develops, the research demand for new formulations such as improvement of the feeling of use and enhancement of the efficacy of pharmaceuticals and cosmetics is increasing. Recently, studies on W/S emulsions using silicone oil with excellent lubricity and release properties and excellent water repellency in a continuous phase are being actively developed in the formulation field. In order to diversify the rheological properties of this W/S emulsion formulation, there is great interest in research on producing W/S Pickering emulsion formulations using plate-shaped nanoparticles with excellent skin affinity and adhesion as functional surfactants and thickeners.

In particular, hectorite having a plate-shaped structure has a large surface area and possesses a high cation exchange capacity, so it is attracting attention as a thickener for oily formulations. Because hectorite forms a three-dimensional plate-shaped network structure by hydrogen bonding between plate edges in oil, it is known that a stable Pickering emulsion may be produced by inducing excellent thickening performance and reversible sol-gel phase transition.

However, in the W/S Pickering emulsion produced using hectorite, the hectorite plate-shaped particles increase the viscosity of the continuous phase to maintain stability, but when the plate-shaped particles adsorb at the droplet interface during emulsification to form an interfacial film, interstitial imperfections occur between particles existing in the droplet interfacial film due to electrostatic repulsive force between particles and geometrical structure of particles. These imperfections eventually lead to the leakage of substances inside the droplets, which negatively affects the structural stability of the W/S Pickering emulsion.

SUMMARY

This section provides a general summary of the disclosure, and is not a comprehensive disclosure of its full scope or all of its features.

An aspect of the present disclosure is directed to providing a composite for forming a coacervate interfacial film capable of forming a stable coacervate interfacial film by electrostatic interaction at the interface between a water phase and an oil phase by providing a cationic hectorite nanoplate particle structure and an anionic cellulose nanofibril.

Another aspect of the present disclosure is directed to providing a Pickering emulsion containing the composite for forming the coacervate interfacial film and a method for producing the same.

Yet another aspect of the present disclosure is directed to providing a cosmetic or drug delivery composition containing the composite for forming the coacervate interfacial film.

The composite for forming the coacervate interfacial film according to an embodiment of the present disclosure contains a cationic hectorite nanoplate particle structure containing a hectorite nanoplate particle and a cationic surfactant coupled to a surface of the hectorite nanoplate particle, and an anionic cellulose nanofibril containing an anionic functional group in at least a portion thereof.

In an embodiment, the composite may form the coacervate interfacial film at an interface of an oil phase and a water phase through electrostatic interaction between the cationic surfactant and the anionic functional group.

In an embodiment, the hectorite nanoplate particle may have an average particle size of 40 nm to 60 nm and a thickness of 8 nm to 10 nm.

In an embodiment, the cationic surfactant may contain a quaternary alkyl ammonium salt.

In an embodiment, the cationic surfactant may include at least one selected from the group consisting of dimethyl dihydrogenated tallow ammonium ion (2M2HT), dimethyl benzyl (hydrogenated tallow) ammonium chloride (2MBHt), trimethyl (hydrogenated tallow) ammonium chloride (3MHt), benzyl dimethyl hydrogenated tallow ammonium ion (2MHTL8), tetramethylammonium hydroxide (TMAH), tetraethylammonium hydroxide (TEAH), tetramethylammonium chloride (TMACl), tetrabutylammonium bromide (TBAB), tetrabutylammonium fluoride (TBAF), and benzyltrimethylammonium hydroxide (BTMAH).

In an embodiment, the anionic functional group may include at least one selected from the group consisting of a substituted or unsubstituted carboxyl group (—COOH, —COONa) and a hydroxymethyl group (—CH$_2$OH).

In an embodiment, at least a portion of the anionic cellulose nanofibrils may penetrate a coacervate interfacial film and exist in an oil phase.

A Pickering emulsion according to an embodiment of the present disclosure may contain: each different liquid, a dispersed phase and a continuous phase; and an anionic cellulose nanofibril and a cationic hectorite nanoplate particle structure that forms a coacervate interfacial film which is located at an interface of the dispersed phase and the continuous phase and lowers an interfacial tension therebetween, in which the cationic hectorite nanoplate particle structure may contain a hectorite nanoplate particle and a cationic surfactant coupled to a surface of the hectorite nanoplate particle, in which the anionic cellulose nanofibril may contain an anionic functional group in at least a portion thereof, and in which the cationic hectorite nanoplate particle structure may be disposed in contact with an oil phase and the anionic cellulose nanofibril may be disposed in contact with a water phase, and may form the coacervate interfacial film by electrostatic interaction between the cationic surfactant and the anionic functional group.

In an embodiment, at least a portion of the anionic cellulose nanofibrils may penetrate a coacervate interfacial film and exist in an oil phase.

In another embodiment of the present disclosure, a method for producing a Pickering emulsion may include:

grafting a cationic surfactant on a surface of hectorite; producing a cationic hectorite nanoplate particle structure by exfoliating the hectorite grafted with the cationic surfactant; and mixing and homogenizing dispersion in which the cationic hectorite nanoplate particle structure is dispersed and an aqueous solution containing an anionic cellulose nanofibril containing an anionic functional group in at least a portion thereof.

In an embodiment, the cationic hectorite nanoplate particle structure may be included in an amount of 0.1 to 5 wt % with respect to dispersion, and the anionic cellulose nanofibril may be included in an amount of 0.1 to 5 wt % with respect to distilled water.

In an embodiment, the cationic surfactant may contain a quaternary alkyl ammonium salt.

In an embodiment, the grafting of the cationic surfactant on the surface of the hectorite may include ion-exchanging an interlayer inorganic cation of hectorite with a cationic surfactant.

In an embodiment, the anionic cellulose nanofibril may be formed by including TEMPO oxidation treating bacterial cellulose, and dispersing a nanofibril of the bacterial cellulose by applying ultrasonic waves to the TEMPO oxidation-treated cellulose.

A cosmetic or drug delivery composition according to an embodiment of the present disclosure may contain: each different liquid, a dispersed phase and a continuous phase; an anionic cellulose nanofibril and a cationic hectorite nanoplate particle structure that forms a coacervate interfacial film which is located at an interface of the dispersed phase and the continuous phase and lowers an interfacial tension therebetween; and an active ingredient contained inside the dispersed phase, in which the cationic hectorite nanoplate particle structure contains a hectorite nanoplate particle and a cationic surfactant coupled to a surface of the hectorite nanoplate particle, in which the anionic cellulose nanofibril contains an anionic functional group in at least a portion thereof, and in which the cationic hectorite nanoplate particle structure is disposed in contact with an oil phase and the anionic cellulose nanofibril is disposed in contact with a water phase, and forms the coacervate interfacial film by electrostatic interaction between the cationic surfactant and the anionic functional group.

According to an embodiment of the present disclosure, a very stable coacervate interfacial film can be formed at the oil-water interface by using the electrostatic interaction between the cationic hectorite nanoplate particle structure and the anionic cellulose nanofibril. Accordingly, it is possible to have a high storage coefficient value by the coacervate interfacial film.

Furthermore, the Pickering emulsion of the present disclosure prevents coalescence between droplets by bridges formed with a portion of anionic cellulose nanofibrils existing in an oil phase as well as increases the viscosity of a continuous phase, so that it is possible to form a stable emulsion system with a reduced diffusion rate as a result by overcoming the instability caused by the imperfection in a film structure of the Pickering emulsion produced with the conventional plate-shaped particles.

Accordingly, by applying a composite for forming a coacervate interfacial film of the present disclosure to a cosmetic or drug delivery composition, cosmetic or drug delivery efficiency can be remarkably improved.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 5A:
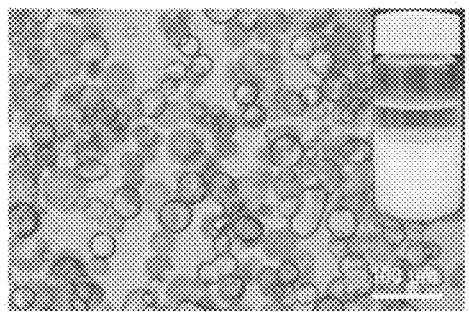
Figure 5B:
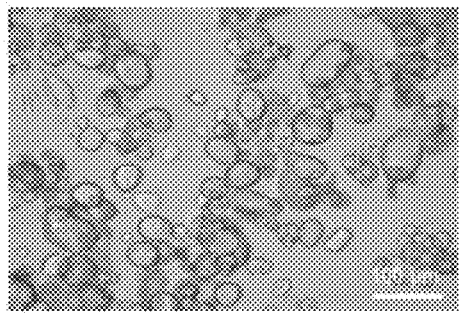
Figure 5C:
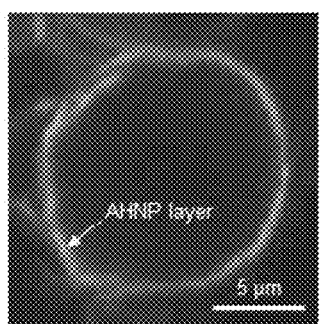
Figure 5D:
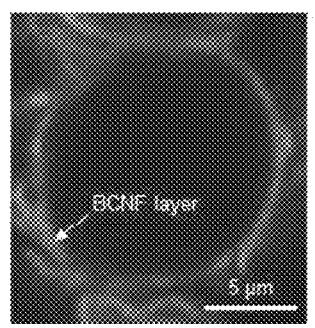
Figure 5E:
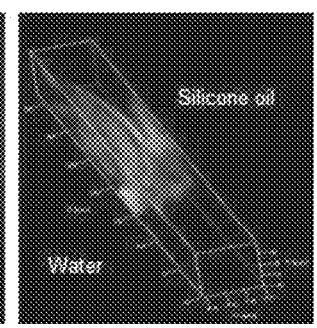

FIG. 5A shows an emulsion stabilized with only the cationic hectorite nanoplate particle structure according to a comparative example, FIG. 5B shows an optical microscope image of a Pickering emulsion according to an example, FIGS. 5C and 5D show confocal laser microscope images of the cationic hectorite nanoplate particle structure and anionic cellulose nanofibril bilayer structure, and FIG. 5E shows a Z-stack three-dimensional confocal laser microscope image of a Pickering emulsion according to an embodiment.

Figure 6A:
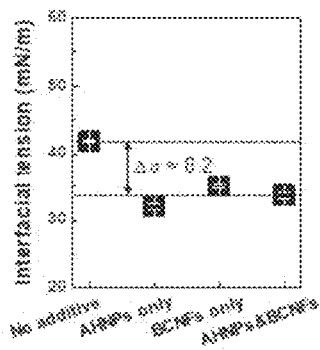
Figure 6B:
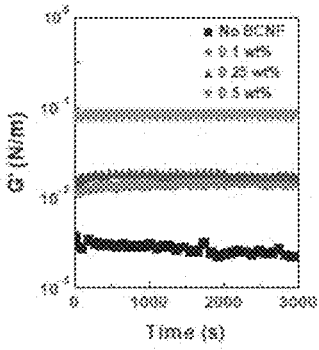
Figure 6C:
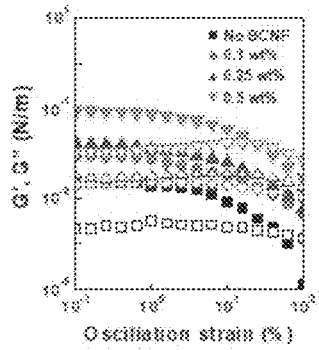

FIG. 6A shows the interfacial tension of each of the cationic hectorite nanoplate particle structure, the anionic cellulose nanofibrils, and the composite for forming a coacervate interfacial film according to an embodiment of the present disclosure, and FIG. 6B and FIG. 6C show the analysis of viscoelastic behavior according to the concentration of anionic cellulose nanofibrils.

Figure 7A:
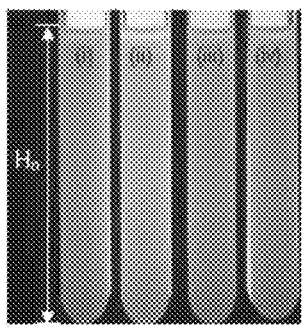
Figure 7B:
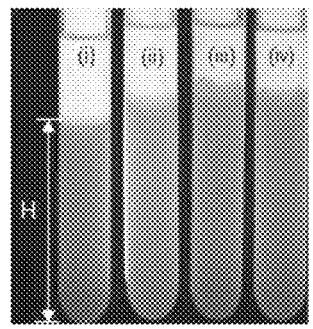
Figure 7C:
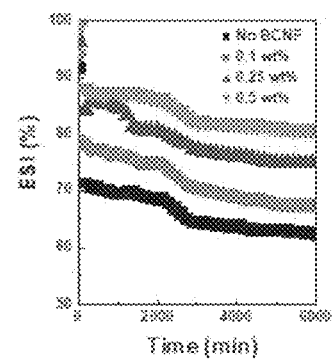

FIG. 7A and FIG. 7B show the sedimentation test results of the W/S Pickering emulsion according to the concentration of cellulose nanofibrils ((A) 0 h, (B) 96 h), and FIG. 7C shows the emulsification stability index according to the storage time (Cellulose nanofibril concentration (i) 0 wt %, (ii) 0.1 wt %, (iii) 0.25 wt %, (iv) 0.5 wt %).

Figure 8A:
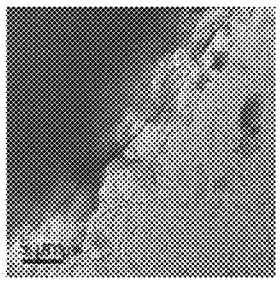
Figure 8B:
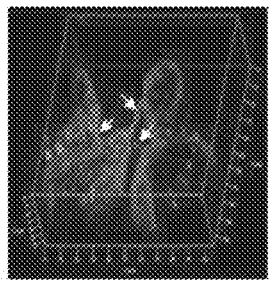
Figure 8C:
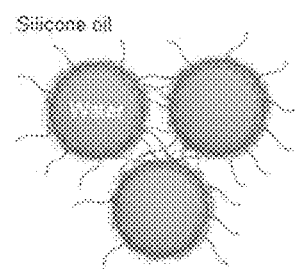
Figure 8D:
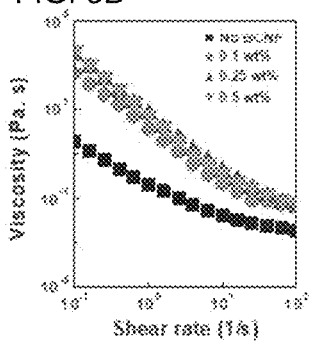
Figure 8E:
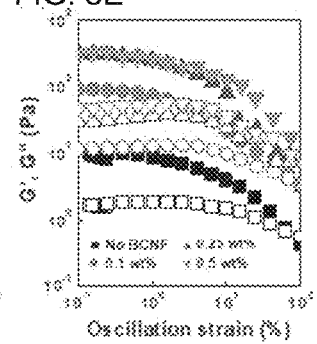
Figure 8F:
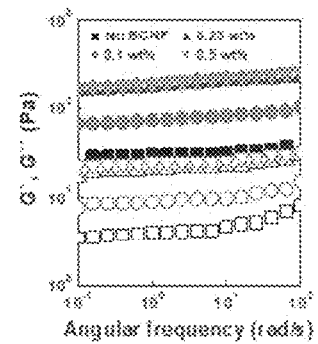

FIG. 8A shows a cellulose nanofibril bridge image through Cryo-HAADF-STEM analysis, FIG. 8B shows a Z-stack three-dimensional confocal laser microscope image of a Pickering emulsion connected by a cellulose nanofibril bridge, FIG. 8C shows a schematic diagram of a Pickering emulsion according to an embodiment of the present disclosure, FIG. 8D shows the viscosity according to the concentration of cellulose nanofibrils, and FIG. 8E and FIG. 8F show the analysis of viscoelastic behavior through comparison of the storage modulus and loss modulus according to the concentration of cellulose nanofibrils.

Corresponding reference numerals indicate corresponding parts or features throughout the several views of the drawings.

DETAILED DESCRIPTION

Example embodiments will now be described more fully with reference to the accompanying drawings.

The present disclosure may be variously modified and have various types, and specific embodiments thereof will be illustrated in the drawings and described in detail in the detailed description. However, this is not intended to limit the present disclosure to specific embodiments, and it should be understood that all modifications, equivalents, and substitutes included in the spirit and technical scope of the present disclosure are included.

The terms used herein are used for description purposes only, and should not be construed as being limited by these embodiments. The terms in singular form may include plural forms unless otherwise specified. It will be understood that the terms "comprising" or "having," when used herein, specify the presence of stated features, integers, steps, operations, elements, components, or combinations thereof, but do not preclude the presence or addition of one or more other features, integers, steps, operations, elements, components, or combinations thereof.

Unless otherwise defined, all technical and scientific terms used in the embodiments have the same meanings as commonly understood by a skilled expert in the technical field to which the present disclosure belongs. It will be further understood that terms, such as those defined in commonly used dictionaries, should be interpreted as having a meaning that is consistent with their meanings of the context of the relevant art and the present disclosure, and will not be interpreted in an idealized or overly formal sense unless expressly so defined herein.

Figure 1:
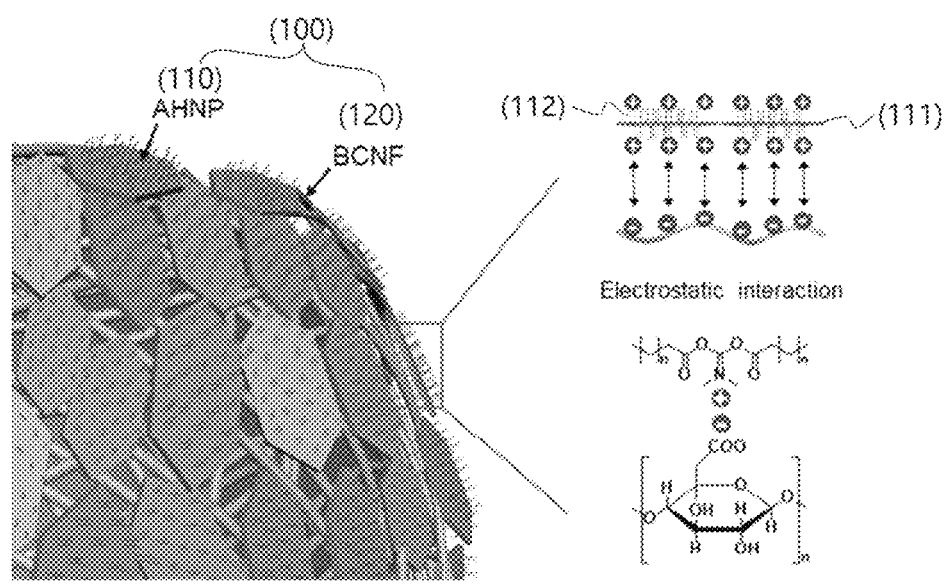
FIG. 1 is a view showing a composite for forming a coacervate interfacial film according to an embodiment of the present disclosure.

FIG. 1 is a view showing a composite for forming a coacervate interfacial film according to an embodiment of the present disclosure.

Referring to FIG. 1, a composite 100 for forming a coacervate interfacial film according to an embodiment of the present disclosure may contain a cationic hectorite nanoplate particle structure 110 and an anionic cellulose nanofibril 120, and may form a coacervate interfacial film at an interface of an oil phase and a water phase through electrostatic interaction.

The cationic hectorite nanoplate particle structure 110 may include a hectorite nanoplate particle 111 and a cationic surfactant 112 coupled to the surface of the hectorite nanoplate particle 111, and the anionic cellulose nanofibril 120 may include an anionic functional group in at least a portion thereof.

The hectorite nanoplate particle 111 is an inorganic material having a large surface area and high cation exchange capacity, and may have an average particle size of about 40 to 60 nm, and a thickness of about 8 to 10 nm. In an embodiment, the hectorite nanoplate particle 111 may be a particle formed by exfoliating hectorite in a high-pressure emulsification method.

As illustrated in FIG. 1, the cationic surfactant 112 causes an electrostatic interaction with an anionic functional group included in the anionic cellulose nanofibril 120 to form a coacervate interfacial film at an interface of an oil phase and a water phase.

In an embodiment, the cationic surfactant 112 is not particularly limited as long as it is a material capable of causing an electrostatic interaction with an anionic functional group, but may preferably contain a quaternary alkyl ammonium salt. For example, the cationic surfactant 112 may include at least one selected from the group consisting of dimethyl dihydrogenated tallow ammonium ion (2M2HT), dimethyl benzyl (hydrogenated tallow) ammonium chloride (2MBHt), trimethyl (hydrogenated tallow) ammonium chloride (3MHt), benzyl dimethyl hydrogenated tallow ammonium ion (2MHTL8), tetramethylammonium hydroxide (TMAH), tetraethylammonium hydroxide (TEAH), tetramethylammonium chloride (TMACl), tetrabutylammonium bromide (TBAB), tetrabutylammonium fluoride (TBAF), and benzyltrimethylammonium hydroxide (BTMAH).

The anionic cellulose nanofibril 120 is a material capable of causing an electrostatic interaction with the cationic surfactant 112, and the anionic functional group included in at least a portion may include at least one selected from the group consisting of a substituted or unsubstituted carboxyl group (—COOH, —COONa) and a hydroxymethyl group (—CH$_2$OH).

In an embodiment, the anionic cellulose nanofibril 120 may be formed by dispersing a nanofibril by applying ultrasonic waves after TEMPO oxidation treatment of bacterial cellulose.

At least a portion of the anionic cellulose nanofibrils 120 may penetrate a coacervate interfacial film and exist in an oil phase. As described above, a portion of the anionic cellulose nanofibrils 120 existing in the oil phase fills the imperfections between the hectorite nanoplate particle structures 110 to improve the structural stability of an emulsion, and provide excellent safety.

Figure 2:
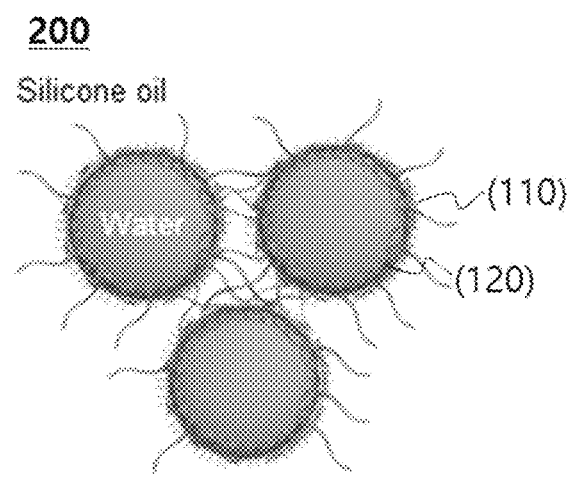
FIG. 2 is a view showing a Pickering emulsion according to an embodiment of the present disclosure.

FIG. 2 is a view showing a Pickering emulsion according to an embodiment of the present disclosure.

Referring to FIG. 2, the Pickering emulsion 200 according to an embodiment of the present disclosure may contain the anionic cellulose nanofibril 120 and the cationic hectorite nanoplate particle structure 110 that forms a coacervate interfacial film that is located in each different liquid, a dispersed phase and a continuous phase, and at the interface of the dispersed phase and the continuous phase and lowers the interfacial tension therebetween.

The emulsion may be an oil-in-water emulsion in which the dispersed phase and the continuous phase are an oil phase and a water phase, respectively, or a water-in-oil emulsion in which the dispersed phase and the continuous phase are a water phase and an oil phase, respectively.

The cationic hectorite nanoplate particle structure 110 and the anionic cellulose nanofibril 120 are substantially the same as the composite 100 for forming the coacervate interfacial film described with reference to FIG. 1, and thus a redundant detailed description thereof will be omitted.

At an interface of the dispersed phase and the continuous phase, the cationic hectorite nanoplate particle structure 110 may be disposed in contact with an oil phase and the anionic cellulose nanofibril 120 may be disposed in contact with a water phase, and the cationic hectorite nanoplate particle structure 110 and the anionic cellulose nanofibril 120 may form a very stable coacervate interfacial film by electrostatic interaction between the cationic surfactant 112 and the anionic functional group.

When the concentration of the anionic cellulose nanofibril 120 inside the droplets remaining after forming the interface increases, the imperfections between the hectorite nanoplate particle structures 110 may be filled in order to balance the thermal equilibrium around the interfacial film. As diffusion migration occurs, at least a portion of the anionic cellulose nanofibrils 120 may penetrate a coacervate interfacial film and exist in an oil phase.

As such, by bridges formed with a portion of the anionic cellulose nanofibrils 120 existing in an oil phase, coalescence between droplets is prevented and the viscosity of a continuous phase is also increased. Accordingly, the Pickering emulsion 200 of the present disclosure may form a stable emulsion system with a reduced diffusion rate.

A method for producing a Pickering emulsion according to an embodiment of the present disclosure may include: grafting a cationic surfactant on a surface of hectorite (S110); producing a cationic hectorite nanoplate particle structure by exfoliating the hectorite grafted with the cationic surfactant (S120); and mixing and homogenizing dispersion in which the cationic hectorite nanoplate particle structure is dispersed and an aqueous solution containing an anionic cellulose nanofibril containing an anionic functional group in at least a portion thereof (S130).

Figure 3A:
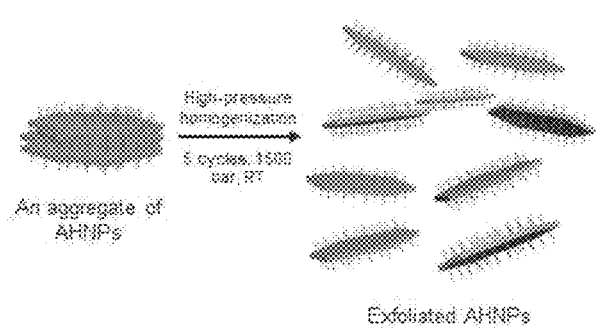
FIG. 3A shows a method for producing a cationic hectorite nanoplate particle structure according to an embodiment of the present disclosure.
Figure 3B:
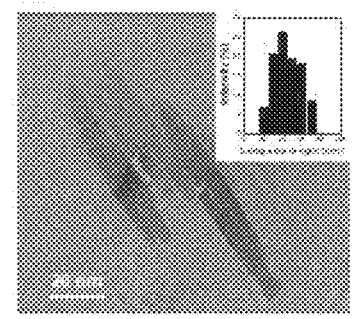
FIG. 3B shows a transmission electron microscope image of the produced cationic hectorite nanoplate particle structure.

FIG. 3A shows a method for producing a cationic hectorite nanoplate particle structure according to an embodiment of the present disclosure, and FIG. 3B shows a transmission electron microscope image of the produced cationic hectorite nanoplate particle structure.

Referring to FIG. 3A, S110 may be performed by ion-exchanging an interlayer inorganic cation of hectorite with a cationic surfactant, but is not limited thereto. In addition, as described above, the cationic surfactant may use a quaternary alkyl ammonium salt, and may preferably include at least one selected from the group consisting of dimethyl dihydrogenated tallow ammonium ion (2M2HT), dimethyl benzyl (hydrogenated tallow) ammonium chloride (2MBHt), trimethyl (hydrogenated tallow) ammonium chloride (3MHt), benzyl dimethyl hydrogenated tallow ammonium ion (2MHTL8), tetramethylammonium hydroxide (TMAH), tetraethylammonium hydroxide (TEAH), tetramethylammonium chloride (TMACl), tetrabutylammonium bromide (TBAB), tetrabutylammonium fluoride (TBAF), and benzyltrimethylammonium hydroxide (BTMAH).

In S120, a cationic hectorite nanoplate particle structure may be produced by exfoliating the hectorite grafted with the cationic surfactant.

In an embodiment, the hectorite may be mechanically exfoliated through a high-pressure emulsification method using a high-pressure homogenizer.

In S130, it is preferable that the cationic hectorite nanoplate particle structure is contained in an amount of 0.1 to 5 wt % with respect to dispersion, and the anionic cellulose nanofibril is contained in an amount of 0.1 to 5 wt % with respect to distilled water. This is because interfacial coacervation is induced within the above-described range to form stable droplets.

When the cationic hectorite nanoplate particle structure is contained in an amount of less than 0.1 wt % with respect to dispersion, the stability of the emulsion is low, and when contained in an amount of more than 5 wt %, the structure forms a network in a continuous phase and is not suitable for coacervation. In addition, when the anionic cellulose nanofibril is contained in an amount of less than 0.1 wt % with respect to distilled water, the stability of the emulsion deteriorates. In addition, it may be identified that a bridge between the droplets is formed due to the extra cellulose from the concentration of 0.5 wt %. However, when the anionic cellulose nanofibril is contained in an amount of more than 5 wt %, the viscosity is high, which causes difficulties in the process.

In one embodiment, the anionic cellulose nanofibril may be produced by dispersing a nanofibril of bacterial cellulose by applying ultrasonic waves to the TEMPO oxidation-treated cellulose after TEMPO oxidation treatment of bacterial cellulose.

According to a composite for forming a coacervate interfacial film, Pickering emulsion, and a method for producing the same according to the present disclosure, a very stable coacervate interfacial film can be formed at the oil-water interface by using the electrostatic interaction between the cationic hectorite nanoplate particle structure 110 and the anionic cellulose nanofibril 120. Accordingly, it is possible to have a high storage coefficient value by the coacervate interfacial film.

Furthermore, it is possible to prevent coalescence between droplets by bridges formed with a portion of anionic cellulose nanofibrils existing in an oil phase as well as increases the viscosity of a continuous phase, so that it is possible to form a stable emulsion system with a reduced diffusion rate as a result by overcoming the instability caused by the imperfection in a film structure of the Pickering emulsion produced with the conventional plate-shaped particle.

Accordingly, when the composite 100 for forming the coacervate interfacial film of the present disclosure is applied to a cosmetic or drug delivery composition, cosmetic or drug delivery efficiency can be remarkably improved.

In other words, in an embodiment of the present disclosure, the Pickering emulsion may be applied to a cosmetic composition or a drug delivery composition.

In this connection, each of the cosmetic composition and the drug delivery composition containing the Pickering emulsion may further contain an active ingredient contained in the dispersed phase.

Hereinafter, in order to help the understanding of the present disclosure, specific examples will be described in detail. However, the following examples are merely some embodiments of the present disclosure, and the scope of the present disclosure is not limited to the following examples.

EXAMPLES

Production of Cationic Hectorite Nanoplate Particle Structures (AHNPs)

To enhance the dispersibility in the silicone oil, hectorite nanoplate particles were mechanically exfoliated and used using a high-pressure emulsification technique (5 cycles, 1500 bar, RT).

First, after hectorite was desorbed by electrostatic repulsive force, the surface was modified by exchanging cations existing in the interlayer with 2M2HT, a cationic surfactant. Then, using a high-pressure emulsification technique using a high-pressure homogenizer, the cationic hectorite nanoplate particle structures were produced by mechanically exfoliating the same at 5 cycles, 1500 bar, and RT conditions.

FIG. 3B shows a transmission electron microscope image of the produced cationic hectorite nanoplate particle structure. Referring to FIG. 3, it was identified that the average particle size of the hectorite nanoplate particles is about 50 nm and the average thickness is about 8 nm.

Figure 4A:
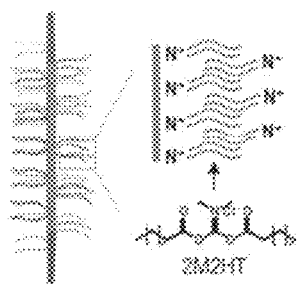
FIG. 4A shows the produced cationic hectorite nanoplate particle structure.
Figure 4B:
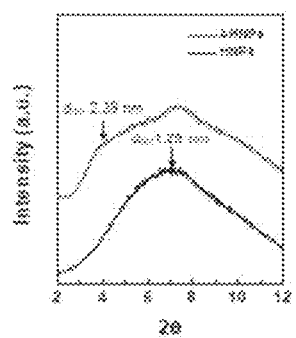
FIG. 4B shows the result of X-ray diffraction analysis.
Figure 4C:
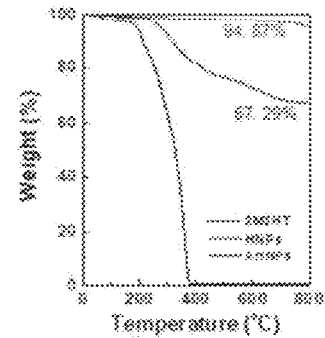
FIG. 4C shows the result of TGA analysis.

FIG. 4A shows the produced cationic hectorite nanoplate particle structure, FIG. 4B shows the result of X-ray diffraction analysis, and FIG. 4C shows the result of TGA analysis.

The presence of the cationic surfactant 2M2HT modified on the surface of the hectorite nanoplate particles was identified from FIGS. 4A to 4C.

Production of Pickering Emulsion through Induction of Coacervation of Cationic Hectorite Nanoplate Particle Structures (AHNPs) and Anionic Cellulose Nanofibril (BCNF)

After mixing 70 wt % of silicone oil in which 0.15 wt % of cationic hectorite nanoplate particle structure is dispersed and 30 wt % of 0.5 wt % of anionic cellulose nanofibril aqueous solution, a Pickering emulsion was produced by inducing coacervation by homogenization at 15,000 rpm for 10 minutes.

Comparative Examples

Except for the cellulose nanofibrils, an emulsion was produced in the same manner as in the above example using only the cationic hectorite nanoplate particle structure.

FIG. 5A shows an emulsion stabilized with only the cationic hectorite nanoplate particle structure according to a comparative example, FIG. 5B shows an optical microscope image of a Pickering emulsion according to an example, FIGS. 5C and 5D show confocal laser microscope images of the cationic hectorite nanoplate particle structure and anionic cellulose nanofibril bilayer structure, and FIG. 5E shows a Z-stack three-dimensional confocal laser microscope image of a Pickering emulsion according to an embodiment.

Referring to FIGS. 5A and 5B, compared to the emulsion (a) of the comparative example formed only with the cationic hectorite nanoplate particle structure, it was observed that in the Pickering emulsion (b) of the example in which anionic cellulose nanofibrils were introduced, the droplet surface was noticeably bumpy due to strong coacervation between hectorite and cellulose, and relatively polygonal droplets were formed.

In addition, as a result of confocal laser microscopy using a fluorescent material that selectively binds to hectorite and cellulose, respectively, as shown in FIGS. 5C and 5D, it was identified that a coacervation bilayer was formed at the oil-water interface. In addition, it was observed that some of the cellulose present inside the droplet is existing in the silicone oil phase, which is a continuous phase. This is because, when the concentration of cellulose inside the droplets remaining after forming the interface increases, imperfections between the hectorite structures are filled in order to achieve thermal equilibrium around the interface film, and diffusion movement occurs. Thus, it can overcome the instability caused by film structural imperfections of the conventional Pickering emulsion and improve the stability of the Pickering emulsion.

Analysis of Interfacial Tension and Interfacial Film Rheological Behavior of Coacervation Bilayers In order to identify the change in the characteristics of the interfacial bilayer formed according to the example, a tensiometer and interfacial rheology analysis were performed, and the results are shown in FIG. 6.

FIG. 6A shows the interfacial tension of each of the cationic hectorite nanoplate particle structure, the anionic cellulose nanofibrils, and the composite for forming a coacervate interfacial film according to an embodiment of the present disclosure, and FIG. 6B and FIG. 6C show the analysis of viscoelastic behavior according to the concentration of anionic cellulose nanofibrils. The viscoelastic behavior analysis was performed by changing only the concentration of the anionic cellulose nanofibrils while the concentration of the hectorite nanoplate particle structure was fixed at 0.15 wt %.

Referring to FIGS. 6A to 6C, the level at which the interfacial tension was reduced by adsorption to the interface did not show a significant difference when compared with the interfacial tension between water and silicone oil, but upon reviewing the results of interfacial rheology analysis, the level of adjusting the film elasticity of the interface showed a significant difference.

Specifically, it was identified that in the case of using only the cationic hectorite nanoplate particle structure (No BCNF), it was not effectively adsorbed to the interfacial film and thus had a low storage coefficient value, whereas in the case of the example of the present disclosure in which cellulose nanofibrils were introduced, the interfacial coacervation bilayer between the two materials had a high storage coefficient value.

In particular, when the concentration of cellulose nanofibrils was 0.5 wt %, it was identified that the interfacial film had viscoelasticity due to additional cellulose nanofibrils that passed through the interfacial film by diffusion, and the storage coefficient value increased by 102 times or more.

Sedimentation Stabilization of Pickering Emulsion According to Concentration of Anionic Cellulose Nanofibrils In order to identify the degree of stabilization of the Pickering emulsion according to the concentration of anionic cellulose nanofibrils, a sedimentation test was performed, and the results are shown in FIGS. 7A to 7B.

Referring to FIG. 7A and FIG. 7B, it was observed that the emulsion gradually settled with time and phase separation occurred. It is schematically shown in FIG. 7C as an ESI (Emulsion stability index) value, which is an index indicating the degree of emulsion phase separation.

Referring to FIG. 7C, it was identified that the ESI value gradually increased as cellulose nanofibrils having concentrations of 0.1, 0.25, and 0.5 wt %, respectively, were introduced into the hectorite nanoplate particle structure fixed at 0.15 wt %. From these results, it was identified that the interfacial characteristics strengthened due to the interfacial bilayer contributed to the stability of the emulsion.

Analysis of Morphology and Rheological Behavior of Pickering Emulsion

FIG. 8A shows a cellulose nanofibril bridge image through Cryo-HAADF-STEM analysis, FIG. 8B shows a Z-stack three-dimensional confocal laser microscope image of a Pickering emulsion connected by a cellulose nanofibril bridge, and FIG. 8C shows a schematic diagram of a Pickering emulsion according to an embodiment of the present disclosure.

As shown in FIGS. 8A to 8C, bridges between droplets formed with extra cellulose nanofibrils existing in the oil phase were identified through Cryo-TEM and CLSM analysis. A more stable Pickering emulsion may be produced by preventing coalescence between droplets due to an increase in the viscosity of a continuous phase due to the bridge between droplets.

Referring to FIG. 8D to FIG., it was identified that the viscosity of the emulsion increased by 102 times or more as the aqueous solution of cellulose nanofibrils having a concentration of 0.1, 0.25, and 0.5 wt %, respectively, was introduced into the hectorite nanoplate particle structure fixed at a concentration of 0.15 wt %. It was identified that the storage coefficient also showed a typical elastic fluid behavior that was increased up to $10^4$ times or more.

Through the analysis of morphology and rheological behavior as above, cellulose nanofibrils existing in a continuous phase form bridges between droplets, affecting the viscoelastic behavior of the continuous phase and lowering the coalescence rate to form a more stable emulsion system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

DESCRIPTION OF REFERENCE NUMERALS

100: COMPOSITE FOR FORMING COACERVATE INTERFACIAL FILM
110: CATIONIC HECTORITE NANOPLATE PARTICLE STRUCTURE
111: HECTORITE NANOPLATE PARTICLE
112: CATIONIC SURFACTANT
120: ANIONIC CELLULOSE NANOFIBRIL
200: PICKERING EMULSION

The invention claimed is:

1. A composite for forming a coacervate interfacial film, the composite comprising:
   a cationic hectorite nanoplate particle structure containing a hectorite nanoplate particle and a cationic surfactant coupled to a surface of the hectorite nanoplate particle; and
   an anionic cellulose nanofibril containing an anionic functional group in at least a portion thereof,
   wherein the composite forms the coacervate interfacial film at an interface of an oil phase and a water phase through electrostatic interaction between the cationic surfactant and the anionic functional group.

2. The composite of claim 1, wherein the hectorite nanoplate particle has an average particle size of 40 nm to 60 nm and a thickness of 8 nm to 10 nm.

3. The composite of claim 1, wherein the cationic surfactant contains a quaternary alkyl ammonium salt.

4. The composite of claim 3, wherein the cationic surfactant includes at least one selected from the group consisting of dimethyl dihydrogenated tallow ammonium ion (2M2HT), dimethyl benzyl (hydrogenated tallow) ammonium chloride (2MBHt), trimethyl (hydrogenated tallow) ammonium chloride (3MHt), benzyl dimethyl hydrogenated tallow ammonium ion (2MHTL8), tetramethylammonium hydroxide (TMAH), tetraethylammonium hydroxide (TEAH), tetramethylammonium chloride (TMACl), tetrabutylammonium bromide (TBAB), tetrabutylammonium fluoride (TBAF), and benzyltrimethylammonium hydroxide (BTMAH).

5. The composite of claim 1, wherein the anionic functional group includes at least one selected from the group consisting of a substituted or unsubstituted carboxyl group (—COOH, —COONa) and a hydroxymethyl group (—CH$_2$OH).

6. The composite of claim 1, wherein at least a portion of the anionic cellulose nanofibrils penetrates a coacervate interfacial film and exists in an oil phase.

7. A Pickering emulsion comprising:
   each different liquid, a dispersed phase and a continuous phase; and
   an anionic cellulose nanofibril and a cationic hectorite nanoplate particle structure that forms a coacervate interfacial film which is located at an interface of the dispersed phase and the continuous phase and lowers an interfacial tension therebetween,
   wherein the cationic hectorite nanoplate particle structure contains a hectorite nanoplate particle and a cationic surfactant coupled to a surface of the hectorite nanoplate particle,
   wherein the anionic cellulose nanofibril contains an anionic functional group in at least a portion thereof, and
   wherein the cationic hectorite nanoplate particle structure is disposed in contact with an oil phase and the anionic cellulose nanofibril is disposed in contact with a water phase, and forms the coacervate interfacial film by electrostatic interaction between the cationic surfactant and the anionic functional group.

8. The Pickering emulsion of claim 7, wherein at least a portion of the anionic cellulose nanofibrils penetrates the coacervate interfacial film and exists in the oil phase.

9. A cosmetic or drug delivery composition comprising:
   each different liquid, a dispersed phase and a continuous phase;
   an anionic cellulose nanofibril and a cationic hectorite nanoplate particle structure that forms a coacervate interfacial film which is located at an interface of the dispersed phase and the continuous phase and lowers an interfacial tension therebetween; and
   an active ingredient contained inside the dispersed phase,
   wherein the cationic hectorite nanoplate particle structure contains a hectorite nanoplate particle and a cationic surfactant coupled to a surface of the hectorite nanoplate particle,
   wherein the anionic cellulose nanofibril contains an anionic functional group in at least a portion thereof, and
   wherein the cationic hectorite nanoplate particle structure is disposed in contact with an oil phase and the anionic cellulose nanofibril is disposed in contact with a water phase, and forms the coacervate interfacial film by electrostatic interaction between the cationic surfactant and the anionic functional group.

10. The cosmetic or drug delivery composition of claim 9, wherein at least a portion of the anionic cellulose nanofibrils penetrates the coacervate interfacial film and exists in the oil phase.

* * * * *